United States Patent [19]

Ishikawa et al.

[11] 4,421,750
[45] Dec. 20, 1983

[54] ORGANOPHOSPHORIC ACID ESTER ANHYDRIDES AS PESTICIDES

[75] Inventors: Hiromichi Ishikawa; Kazuhiko Kitaori, both of Atsugi; Kimiyoshi Kaneko, Isehara; Satoru Moriyama, Ebina; Takashi Kobayashi; Tsugio Uchiyama, both of Atsugi, all of Japan

[73] Assignee: Hokko Chemical Industry Co., Ltd., Nihonbashi, Japan

[21] Appl. No.: 353,927

[22] Filed: Mar. 2, 1982

[30] Foreign Application Priority Data

Mar. 9, 1981 [JP] Japan .................. 56-33295

[51] Int. Cl.³ .................. A01N 57/12; C07F 9/24
[52] U.S. Cl. .................. 424/207; 260/933
[58] Field of Search .................. 260/933; 424/207

[56] References Cited

FOREIGN PATENT DOCUMENTS 2054189 5/1972 Fed. Rep. of Germany ...... 260/933
3208193 9/1982 Fed. Rep. of Germany .

Primary Examiner—Anton H. Sutto
Attorney, Agent, or Firm—Larson and Taylor

[57] ABSTRACT

New organophosphoric acid ester anhydride derivatives, more particularly new thiopyrophosphoric acid P,P,P'-trialkylester-P'-dialkylamide of the formula

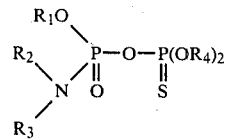

wherein $R_1$ is an alkyl group of 3 to 6 carbon atoms and $R_2$, $R_3$ and $R_4$ may be the same or different from each other and each are an alkyl group of 1 to 6 carbon atoms are now provided. These new organophosphoric acid ester anhydride derivatives have high insecticidal, miticidal and nematocidal activities and are useful as an insecticidal, miticidal and nematocidal agent.

7 Claims, No Drawings

ORGANOPHOSPHORIC ACID ESTER ANHYDRIDES AS PESTICIDES

BACKGROUND OF THE INVENTION

1. Field of the Invention

This invention relates to new organophosphoric acid ester anhydride derivatives and, more particularly, to new thiopyrophosphoric acid P,P,P'-trialkylester-P'-dialkylamide having a high insecticidal activity, high miticidal activity and high nematocidal activity in combination. This invention also relates to a process for the production of these new organophosphoric acid ester anhydride derivatives, as well as to an insecticidal, miticidal and nematocidal composition containing the above-mentioned new compound as active ingredient.

2. Description of the Prior Art

Many kinds of the organo-phosphorus compounds having the insecticidal activity, miticidal activity and/or nematocidal activity are known. For instance, thiopyrophosphoric acid P,P,P'-triethylester-P'-dimethylamide of the formula

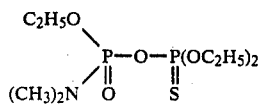

thiopyrophosphoric acid P,P,P'-triethylester-P'-diethylamide of the formula

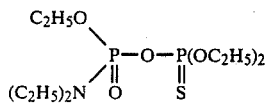

and dithipyrophosphoric acid P,P,P'-triethylester-P'-dimethylamide of the formula

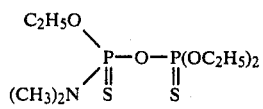

are known to have the insecticidal activity, as described in the "Izvestiia Akademii Nauk SSSR" pp. 1038–1041 (1954) and the "Khim i Primerenie" pp. 164–175 (1955). Furthermore, pyrophosphoric acid P,P,P'-triethylester-P'-dimethylamide is known to have the insecticidal activity, as described in the "Chemical Abstracts" Vol. 61 (1964) 8832 g and in the "Aspirantsk Roboty Nauchn" pp. 66–69 (1963). In Japanese patent application unexamined prepublication "Kokai" Sho 47-9600 (corresponding to German DT-OS 2054189), there is described that an organo-phosphorus compound of the formula

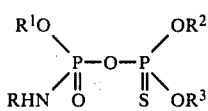

wherein $R^1$, $R^2$ and $R^3$ may be the same or different from each other and each are an alkyl group of 1–6 carbon atoms and R is a hydrogen atom, an alkyl group containing up to 6 carbon atoms or phenyl group which may be substituted with a halogen, nitro group and/or alkyl group exhibits an insecticidal activity. Besides, Japanes patent application unexamined prepublication "Kokai" Sho 53-59627 (corresponding to U.S. Pat. No. 4,110,440) discloses that an organophosphoric acid ester anhydride derivative of the general formula

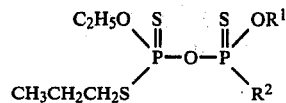

wherein $R^1$ is a lower alkyl group of 1–6 carbon atoms and $R^2$ is an alkoxyl group, alkylthio group, alkylamino group or dialkylamino group exhibits insecticidal, miticidal and nematocidal activities.

Amongst the insect pests, rice stem borer, brown planthoppers, rice leafhoppers, common cutworms and aphids may be mentioned as the main insect pests which are predominantely infesting aquatic rice plants cultivated in the submerged field or the crops cultivated in upland fields in recent years. For the purpose of combating these main insect pests, there have been applied large quantities of insecticides of the organo-phosphorus compound type, insecticides of the carbamate compound type, insecticides of the chlorinated compound type and others since a long time ago. In these years, there occurs an objectionable phenomena that the main insect pets have gained a resistance against the known insecticidal compounds which have extensively been used in the crop fields.

SUMMARY OF THE INVENTION

An object of this invention is to provide a new insecticide of organophosphorus compound type to which the resistance is not yet gained by the main insect pests of the crop fields. Another object of this invention is to provide a new insecticide of organophosphorus compound type which exhibits a higher insecticidal activity than that of the organophosphorus insecticides conventionally used in the crop fields. Further objects of this invention will be clear from the following descriptions.

We, the present inventors, have synthetized a number of new organophosphoric acid esters and studied the physiological properties of them. As a result, we have now found that, amongst the new organophosphoric acid esters synthetized by us, the compound of the general formula

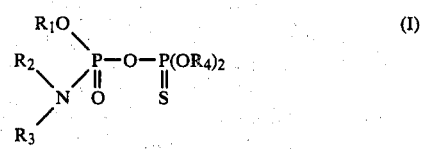

wherein $R_1$ is a lower alkyl group containing 3 or more carbon atoms and $R_2$, $R_3$ and $R_4$ may be the same or different from each other and each are a lower alkyl group exhibits a high insecticidal activity, a high miticidal activity and a high nematocidal activity in combination, and that the new compound of the above formula (I) shows a remarkably high insecticidal activity against the "resistant" strains of insect pests such as green rice leafhopper which have developed the resistance to various kinds of the known organophosphorus type insecticides and of the known carbamate-type insecticides.

According to a first aspect of this invention, therefore, there is provided as the new compound an organophosphoric acid ester anhydride derivative of the general formula

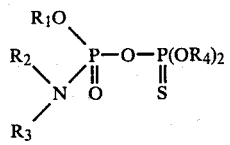

(I)

wherein $R_1$ is a lower alkyl group containing 3 or more carbon atoms and $R_2$, $R_3$ and $R_4$ may be the same or different from each other and each are a lower alkyl group.

According to a preferred embodiment of the first aspect of this invention, there is provided a new compound of the general formula

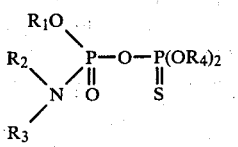

(I')

wherein $R_1$ is an alkyl group containing 3 or 4 carbon atoms and $R_2$, $R_3$ and $R_4$ may be the same or different from each other and each are an alkyl group containing 1 to 4 carbon atoms. In this specification, the term "a lower alkyl group" means "an alkyl group containing 1 to 6 carbon atoms", except that otherwise stated. The term "organophosphoric acid ester anhydride derivative" used to represent the new compound of the general formula (I) or (I') may also be termed as "thiopyrophosphoric acid P,P,P'-trialkylester-P'-dialkylamide".

According to another preferred embodiment of this first aspect invention, there is provided the new compound of the formula (I) or (I') where $R_1$ is n-propyl, isopropyl, n-butyl or isobutyl, $R_2$ is methyl, ethyl or n-propyl, $R_3$ is methyl, ethyl, n-propyl, isopropyl or n-butyl, and $R_4$ is methyl, ethyl, n-propyl, isopropyl or n-butyl.

According to a further preferred embodiment of the first aspect invention, there is provided the new compound of the formula (I) or (I') where $R_1$ is n-propyl or isopropyl, $R_2$ is methyl or ethyl, $R_3$ is methyl or ethyl, and $R_4$ is ethyl.

Although the new compound of the general formula (I) or (I') according to this invention has a chemical structure similar to that of the known pyrophosphoric acid P,P,P'-trialkylester-P'-alkylamides of the chemical literatures hereinbefore mentioned, it has been found that the new compound of this invention is remarkably superior to the known, similar compounds in the insecticidal activity, miticidal activity and nematocidal activity. Besides, it is observed that the pesticidal activities of the new compound of this invention are much more rapid and lasting than those of the known, similar compounds of the above-mentioned literatures. In addition to that the new compound of this invention exhibits the excellent, insecticidal, miticidal and nematocidal activities, the new compound of this invention advantageously exhibits no or little toxicity to mammalian animals and does not exhibit any phyto-toxicity to crop plants at all.

Representative examples of the new compounds of the formula (I) or (I') according to this invention are listed in Table 1 below, together with the structural formulae and optical refractive index of them.

TABLE 1

| Compound No. | Structure formula | Refractive Index |
|---|---|---|
| 1. | n-C$_3$H$_7$O\P(=O)(N(CH$_3$)$_2$)—O—P(=S)(OCH$_3$)$_2$ | $n_D^{23} = 1.4623$ |
| 2. | n-C$_3$H$_7$O\P(=O)(N(CH$_3$)$_2$)—O—P(=S)(OC$_2$H$_5$)$_2$ | $n_D^{25} = 1.4557$ |
| 3. | n-C$_3$H$_7$O\P(=O)(N(CH$_3$)$_2$)—O—P(=S)(OC$_3$H$_7$—n)$_2$ | $n_D^{25} = 1.4511$ |
| 4. | n-C$_3$H$_7$O\P(=O)(N(CH$_3$)$_2$)—O—P(=S)(OC$_3$H$_7$—i)$_2$ | $n_D^{25} = 1.4509$ |
| 5. | n-C$_3$H$_7$O\P(=O)(N(CH$_3$)$_2$)—O—P(=S)(OC$_4$H$_9$—n)$_2$ | $n_D^{25} = 1.4502$ |
| 6. | n-C$_3$H$_7$O\P(=O)(N(CH$_3$)(C$_2$H$_5$))—O—P(=S)(OC$_2$H$_5$)$_2$ | $n_D^{25} = 1.4502$ |
| 7. | n-C$_3$H$_7$O\P(=O)(N(CH$_3$)(n-C$_3$H$_7$))—O—P(=S)(OC$_2$H$_5$)$_2$ | $n_D^{23} = 1.4518$ |
| 8. | n-C$_3$H$_7$O\P(=O)(N(CH$_3$)(i-C$_3$H$_7$))—O—P(=S)(OC$_2$H$_5$)$_2$ | $n_D^{23} = 1.4503$ |
| 9. | n-C$_3$H$_7$O\P(=O)(N(CH$_3$)(n-C$_4$H$_9$))—O—P(=S)(OC$_2$H$_5$)$_2$ | $n_D^{23} = 1.4498$ |
| 10. | n-C$_3$H$_7$O\P(=O)(N(C$_2$H$_5$)$_2$)—O—P(=S)(OCH$_3$)$_2$ | $n_D^{25} = 1.4595$ |
| 11. | n-C$_3$H$_7$O\P(=O)(N(C$_2$H$_5$)$_2$)—O—P(=S)(OC$_2$H$_5$)$_2$ | $n_D^{25} = 1.4526$ |
| 12. | n-C$_3$H$_7$O\P(=O)(N(n-C$_3$H$_7$)$_2$)—O—P(=S)(OC$_2$H$_5$)$_2$ | $n_D^{25} = 1.4487$ |

TABLE 1-continued

| Compound No. | Structure formula | Refractive Index |
|---|---|---|
| 13. | i-C$_3$H$_7$O\\P—O—P(OC$_2$H$_5$)$_2$ ; (CH$_3$)$_2$N/ ‖ O ‖ S | $n_D^{23} = 1.4551$ |
| 14. | n-C$_4$H$_9$O\\P—O—P(OCH$_3$)$_2$ ; (CH$_3$)$_2$N/ ‖ O ‖ S | $n_D^{23} = 1.4600$ |
| 15. | n-C$_4$H$_9$O\\P—O—P(OC$_2$H$_5$)$_2$ ; (CH$_3$)$_2$N/ ‖ O ‖ S | $n_D^{25} = 1.4569$ |
| 16. | n-C$_4$H$_9$O\\ CH$_3$\\P—O—P(OC$_2$H$_5$)$_2$ ; N/ ‖ O ‖ S ; C$_2$H$_5$ | $n_D^{25} = 1.4514$ |
| 17. | n-C$_4$H$_9$O\\P—O—P(OC$_2$H$_5$)$_2$ ; (C$_2$H$_5$)$_2$N/ ‖ O ‖ S | $n_D^{25} = 1.4511$ |
| 18. | i-C$_4$H$_9$O\\P—O—P(OC$_2$H$_5$)$_2$ ; (CH$_3$)$_2$N/ ‖ O ‖ S | $n_D^{23} = 1.4550$ |
| 19. | i-C$_4$H$_9$O\\P—O—P(OC$_2$H$_5$)$_2$ ; (C$_2$H$_5$)$_2$N/ ‖ O ‖ S | $n_D^{23} = 1.4522$ |

The new compound of the general formula (I) or (I') according to this invention can be produced by a process which is shown by the following reaction equation:

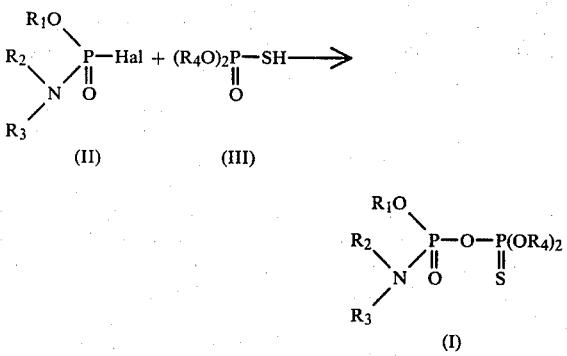

in which R$_1$ is a lower alkyl group containing 3 or more carbon atom and R$_2$, R$_3$ and R$_4$ are each a lower alkyl group and Hal denotes a halogen atom such as chlorine or bromine.

According to a second aspect of this invention, therefore, there is provided a process for the production of an organophosphoric acid ester anhydride derivative of the general formula

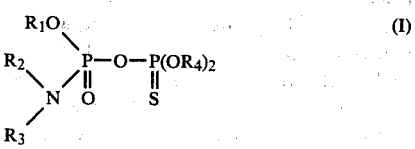

wherein R$_1$ is a lower alkyl group containing 3 or more carbon atoms and R$_2$, R$_3$ and R$_4$ may be the same or different from each other and each are a lower alkyl group, which comprises:

reacting an amidophosphoryl halide of the general formula

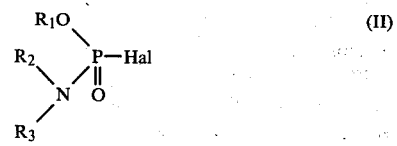

wherein R$_1$, R$_2$ and R$_3$ are as defined above and Hal is a halogen atom such as chlorine or bromine, with an alkali metal salt or ammonium salt of a phosphorothioate of the general formula

wherein R$_4$ is as defined above, in an inert organic solvent at a temperature of 0° to 120° C.

The phosphoric acid derivatives of the general formulae (II) and (III) are the known compounds and can be prepared by known methods described in certain chemical literatures. The phosphoric acid derivative of the general formula (III) is used either in the form of an alkali metal salt such as sodium, potassium or lithium salt or in the form of the ammonium salt. In the process of this invention, the reaction may be conducted in the presence of an acid-binding agent, if required. The acid-binding agent available for this purpose includes an alkali metal hydroxide, carbonate or hydrogen carbonate; an alkali metal alcoholate such as sodium methoxide or sodium ethoxide; a tertiary amine such as triethylamine, diethylamine, pyridine and the like which have been employed conventionally as the acid-binding agents.

The reaction is conducted preferably in an inert organic solvent which may be, for example, an aliphatic or aromatic hydrocarbon such as benzene, toluene, xylene, kerosine; chlorinated aliphatic or aromatic hydrocarbon such as methylene chloride, chloroform, carbon tetrachloride, chlorobenzene; ethers such as diethylether, dibutylether, dioxane; ketones such as acetone, methyl ethyl ketone, methyl isopropyl ketone, methyl isobutyl ketone; or nitriles such as acetonitrile and propionitrile. The reaction temperature may vary within a wide range and usually be in a range of 0° C. to 120° C. and preferably in a range of 20° C. to 80° C. The reaction may proceed under atmospheric pressure, though the reaction may be conducted under an elevated pressure, if desired. The reactants of the formulae (II) and (III) may preferably be present in a substantially equimolar or equimolar proportion in the reaction mixture.

The new compounds of this invention are effective to combat a wide variety of the insect pests such as the insects sucking as the bait the body juice of plants or animals; and the insects chewing a portion of plants or animals or a material of vegetable or animal origin, as well as the acarine pests and nematodes. The insect and acarine pests which may be combated with the new compounds of this invention include those associated with agriculture (including the growing of crops for food and fibre, horticulture and animal husbandry), such as the insect and acarine pests infesting the growing plants, those associated with forestry, the storage of products of vegetable origin, such as grains, fruits and timber, and also the pests associated with the transmission of diseases of man and animals, such as houseflies and mosquitos. The new compounds of this invention are useful to combat a wide variety of the insect and acarine pests as mentioned below.

Thus, the pests which may be combated with the new compounds of this invention include: Coleoptera insect pests such as azuki bean weevil (*Callosobruchus chinensis*), maize weevil (*Sitophilus zeamais*), red flour beetle (*Tribolium castaneum*), twenty-eight-spotted ladybird (*Henosepilachna vigintioctopunctata*) and barley wireworm (*Agriotes fuscicollis*); Lepidopterous insect pests such as gypsy moth (*Lymantria dispar*), common cabbageworm (*Pieris rapae*), common cutworm (*Spodoptera litura*), rice stem borer (*Chilo suppressalis*), summer fruit tortrix (*Adoxophyes orana fasciata*) and almond moth (*Ephestia cautella*); Hemipterous insect pests such as green rice leafhopper (*Nephotettix cincticeps*), brown rice planthopper (*Nilaparvata lugens*), comstock mealybug (*Pseudococcus comstocki*), green peach aphid (*Myzus persicae*), and apple aphid (*Aphis pomonella*); Orthopterous insect pests such as German cockroach (*Blatella germanica*), American cockroach (*Periplaneta americana*), and African mole cricket (*Gryllotalpa africana*); Dipterous insect pests such as house fly (*Musca domestica*), yellow-fever mosquito (*Aedes aegypti*), seedcorn maggot (*Hylemya platura*) and smaller house mosquito (*Culex tritaeniorhynchus*). The acarine pests which may be combated with the new compounds of this invention include: carmine spider mite (*Tetranychus cinnabarinus*), two-spotted spider mite (*Tetranychus urticae*), citrus red mite (*Panonychus citri*) and pink citrus rust mite (*Aculops plekassi*) and the like. The nematodes which may be combated with the new compound of this invention include: sourthern root-knot nematode (*Meloidogyne incognita*), rice white-tip nematode (*Aphelenchoides besseyi*), soybean cyst nematode (*Heterodera glycines*) and others.

In use, the new compounds of this invention may be applied to the pests, to the locus of the pests, to the habitate of the pests, or to growing plants liable to infestitation by the pests, by any of the known means of applying the pesticidal compounds, for example, by dusting or spraying. The new compounds of this invention may be formulated into conventional formulations or preparations for pesticidal usage, by mixing the active compound of this invention with an acceptable known diluent or carrier material.

According to a third aspect of this invention, therefore, there is provided an insecticidal, miticidal and nemtocidal composition, comprising an insecticially, miticidally and/or nematocidally effective amount of the organophosphoric acid ester anhydride derivative of the general formula

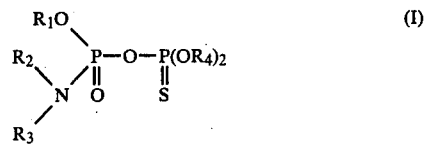

wherein $R_1$ is a lower alkyl group containing 3 or more carbon atoms and $R_2$, $R_3$ and $R_4$ may be the same or different from each other and each are a lower alkyl group, as the active ingredient, in combination with an acceptable diluent or carrier. The compound of the formula (I) which is used in the composition of this invention may preferably be the new compound of the general formula (I') shown hereinbefore.

The pesticidal (insecticidal, miticidal and nematocidal) composition of this invention may be prepared by formulating the new compound of the general formula (I) into the form of emulsifiable concentrate, wettable powder, flowable powder, dusting powder, driftless (DL-type) powder, small granules or granules etc., according to conventional formulation technique. The carrier material which may be admixed with the active compound of this invention may be any solid or liquid ones which have been used conventionally in the preparations for agricultural and horticultural usages. The available carrier in the composition of this invention is not limited to any particular one. The solid carrier available includes, for example, talc, clay, kaolin, silica, diatomaceous earch, bentonite and the like. The liquid carrier includes, for example, xylene, methylnaphthalene, cyclohexane and other suitable organic solvent. Of course, this invention is not limited to the use of these particular carrier materials.

More particularly, the composition of this invention may be in the form of dusting powder in which the active compound is mixed with a solid carrier such as kaolin, bentonite, or it may be in the form of granules in which the active compound is absorbed in a porous granular material such as pumice.

The composition of this invention may also be in the form of liquid preparations to be used as dips or sprays, which are usually aqueous dispersion or emulsion of the active ingredient compound of this invention together with one or more of the known wetting agents, dispersing agents or emulsifying agents.

Wetting agents, dispersing agents and emulsifying agents may be of the cationic, anionic or non-ionic type. Suitable agents of the cationic type may be, for example, quaternary ammonium compounds, for example, cetyltrimethyl ammonium bromide. Suitable agents of the anionic type may be, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and the sodium salts of diisopropyl- or triisopropylnaphthalene sulphonates. Suitable agents of the non-ionic type may be, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters of long chain fatty acids and hexitol anhydrides and the condensation products of the said partial esters with ethylene oxide.

The compositions to be used as sprays may also be in the form of aerosols wherein the formulation is charged in a container under pressure in the presence of a propellant such as fluorotrichloromethane or dichlorodifluoromethane. The compositions which are to be used in the form of aqueous dispersions or emulsions are generally supplied in the form of a concentrate containing a high proportion of the active ingredient compound, and said concentrate may be diluted with water before use. These concentrates are often required to withstand storage for prolonged periods and after such storage, to be capable of dilution with water to form aqueous preparations which remain homogeneous for a sufficient time to enable them to be applied by conventional spary equipment. The concentrates may contain 0.5–90% by weight of the active ingredient compound. When diluted to form aqueous preparations, such preparations may contain varying amounts of the active ingredient depending upon the purpose for which they are to be used.

For agricultural or horticultural purposes, an aqueous preparation containing between 0.0005% and 0.1% by weight of the active compound of this invention is particularly useful.

Generally, the composition of this invention may comprise any of the additive which are conventionally employed in the formulations of agricultural and horticultural usages, such as emulsifying agents, wetting agents, extending agents, dispersion agents and degradation-preventors, by which the effects of the composition as applied can be sured for the intended pesticidal purposes. The composition of this invention may additionally be admixed with a further insecticide, miticide, nemotocide, fungicide and/or herbicide, if desired.

An advantage of the new compound or composition of this invention is that it provides a complete or substantially complete control of the insect and acarine pests with lower rates of the application of the active compound of the formula (I) than are required when the known pyrophosphoric acid P,P,P'-trialkylester-P'-alkylamides of the hereinbefore-mentioned literatures are applied. Particularly, this applies to when the composition of this invention is used to control "resistant" strain of the insects which are substantially not affected by application of the known insecticides of the organophosphorous compound type, because such "resistant" strain of the insects have developed an ability to detoxify the known organophosphorus insecticides through metabolism.

A further advantage of the new compound or composition of this invention is lying in that it is further able to provide complete or substantially complete control of acarine pests of plants. It frequently happens that a growing crop is infested both with the insect pests and with the acarine pests, of example, caterpillars and mites in vegetables such as tomato, when an insecticide and an acaricide both have to be used to provide adequate control of these pests of the different families. However, no separate acaricide is required when the new compound or composition of this invention is used, as the new compound or composition of this invention has a broad spectrum of activity extending not only to the insecticidal properties but also to the acaricidal properties.

According to a further aspect of this invention, there is provided a method of combating insect pests, acarine pests and/or nematode pests at a locus of infestation, which comprise treating the pests or the locus of infestation with an insecticidally, miticidally or nematocidally effective amount of the compound of the general formula (I) or (I').

The invention is now illustrated with reference to the following Examples. Examples 1 and 2 are illustrative of the production of the new compounds of this invention; Examples 3–6 illustrative of the formulations comprising the new compound of this invention; and Examples 7–14 are illustrative of the pesticidal properties of the new compounds of this invention.

EXAMPLE 1

Production of Compound No. 1 of the formula

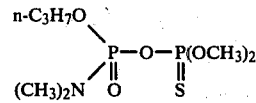

O-n-Propyl-N,N-dimethylamidophsophoryl chloride (18.6 g) of the formula

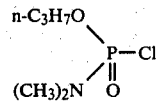

and O,O-dimethyl thiophosphate potassium salt (18.0 g) of the formula

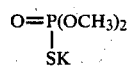

were admixed with 50 ml of acetone, and the resulting admixture was refluxed for 2 hours under stirring. The reaction solution obtained was poured into 300 ml of water and the resulting aqueous mixture was extracted with 100 ml of benzene. The extract in benzene was washed with 5% aqueous sodium carbonate and then with water and dried over anhydrous sodium sulfate, followed by distillation to remove the benzene therefrom. Thiopyrophosphoric acid P,P-dimethyl-P'-n-propyl-P'-dimethylamide of the above formula was afforded as a yellow colored oil in a yield of 27.3 g (74% yield). This oil was isolated and purified in a silica gel column chromatography to give the above-titled compound as a faintly yellow colored oil which showed a refractive index of $n_D^{23} = 1.4623$.

EXAMPLE 2

Production of Compound No. 2 of the formula

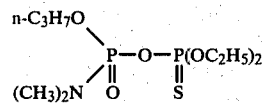

O-n-Propyl-N,N-dimethylamidophosphoryl chloride (18.6 g) and (O,O-diethyl thiophosphate ammonium salt (18.7 g) were admixed with 50 ml of acetone, and the admixture was refluxed for the reaction and then processed in the same manner as in Example 1 to afford thiopyrophosphoric acid P,P-diethyl-P'-n-propyl-P'-dimethylamide in a yield of 30.4 g (95% yield) as a yellow colored oil. This oil was purified and isolated by a silica gel column chromatography to give the titled compound as a yellow colored oil which showed a refractive index of $n_D^{25}=1.4557$.

EXAMPLE 3

Emulsifiable concentrate

40 Parts (by weight) of the Compound No. 2 prepared in the Example 2, 20 parts (by weight) of an emulsifying agent consisting of the condensation product of ethylene oxide with fatty alcohols (available as a tradename "Solpol 700H", a product of Toho Chemical Industry Company, Japan), and 40 parts (by weight) of xylene were mixed together uniformly to give an emulsifiable concentrate which may be diluted with water upon use to give a sprayable emulsion.

EXAMPLE 4

Wettable powder

25 Parts (by weight) of the Compound No. 14 listed in Table 1, 15 parts (by weight) of white carbon (finely divided silica), 3 parts (by weight) of calcium ligninesulfonate, 2 parts (by weight) of a polyoxyethylenenonylphenylether as the non-ionic emulsifier, 5 parts (by weight) of diatomaceous earth and 50 parts (by weight) of clay were ground together and mixed uniformly with each other in a mixer to give a wettable powder which may be dispersed in water upon use.

EXAMPLE 5

Dusting powder 1.5 Parts (by weight) of the Compound No. 1 prepared in the Example 1, was mixed well with 98.5 parts (by weight) of clay, followed by grinding to small particle size. A dusting powder was obtained, which was directly be applied by a known dusting device.

EXAMPLE 6

Granules

5 Parts (by weight) of the Compound No. 2, 1.5 parts (by weight) of lauryl sulfate, 1.5 parts of calcium ligninesulfonate and 67 parts of kaolin were admixed with 15 parts (by weight) of water, followed by kneading in a kneader and granulation in a granulator. The granules so shaped were then dried in a fluidizing drier to give granules which may directly be applied to the soil.

EXAMPLE 7

This Example illustrates the test of estimating the insecticidal activity of test compounds against rice stem borer.

Aquatic rice plants of average height of about 50 cm which had been grown in a pot having an area of 1/10,000 ares at the soil surface were infested with 30 larvae of rice stem borer (*Chilo suppressalis*) which had just hatched from the eggs. 5 Days after the infestation, the rice plants and the larvae were sprayed with the composition under test which was prepared by diluting with water the wettable powder of this invention made according to the preceding Example 4 to the concentration of the active compound as indicated in Table 2 below. The composition was sprayed by means of a spray-gun and was applied at the rate of application of 50 ml per three pots. 5 Days after the spraying, the rice plants were dissected and the numbers of the dead larvae and the surveying larvae were counted, respectively, and percent of mortality was assessed. The tests were conducted with three replicates for a particular value of the concentration of the active compound under test, and the average of % mortality was calculated. The results (expressed as averaged % mortality) are set out in Table 2 below.

TABLE 2

| Test Compounds | Mortality (%) Concentration of active compound sprayed (ppm) | |
|---|---|---|
| | 100 | 50 |
| Compound No. 1 | 100 | 100 |
| Compound No. 2 | 100 | 100 |
| Compound No. 3 | 100 | 100 |
| Compound No. 4 | 100 | 95 |
| Compound No. 5 | 100 | 93 |
| Compound No. 6 | 100 | 100 |
| Compound No. 7 | 100 | 100 |
| Compound No. 8 | 100 | 95 |
| Compound No. 9 | 100 | 93 |
| Compound No. 10 | 100 | 95 |
| Compound No. 11 | 100 | 100 |
| Compound No. 12 | 100 | 93 |
| Compound No. 13 | 100 | 100 |
| Compound No. 14 | 100 | 95 |
| Compound No. 15 | 100 | 100 |
| Compound No. 16 | 100 | 95 |
| Compound No. 17 | 100 | 93 |
| Compound No. 18 | 100 | 95 |
| Compound No. 19 | 100 | 93 |
| Comparative Compound A | 78 | 35 |
| Comparative Compound B | 100 | 60 |
| Comparative Compound C | 60 | 27 |
| Comparative Compound D | 100 | 55 |
| Comparative Compound E | 100 | 56 |
| Comparative Compound F | 100 | 60 |
| Comparative Compound G | 100 | 63 |
| Comparative Compound H | 80 | 30 |
| Comparative Compound I | 100 | 44 |
| Comparative Compound J | 100 | 67 |
| Comparative Compound K | 100 | 57 |
| Comparative Compound L | 100 | 47 |
| Comparative Compound M | 100 | 63 |
| No treatment (Control) | 0 | |

Compound Nos. 1 to 19 as above are identical to those listed in Table 1 before. The same reference is made in the following tables in this specification.

Comparative Compound A:

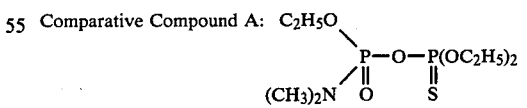

(see "Izuvestiia Akademii Nauk SSSR" pp. 1038-1041 (1954) mentioned hereinbefore)

Comparative Compound B:

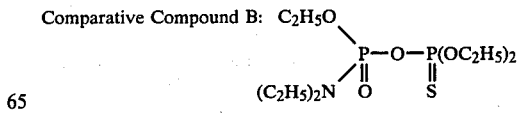

(see "Izuvestiia Akademii Nauk SSSR" pp. 1038-1041 (1954) mentioned hereinbefore)

-continued

Comparative Compound C: 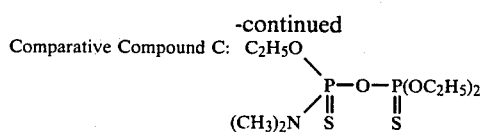

(see "Izuvestiia Akademii Nauk SSSR" pp. 1038-1041 (1954) mentioned hereinbefore)

Comparative Compound D: 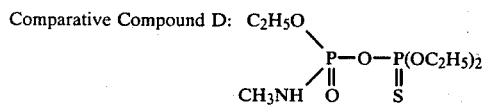

(see German DT-OS 2054189)

Comparative Compound E: 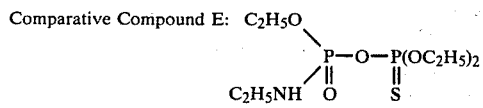

(see German DT-OS 2054189)

Comparative Compound F: 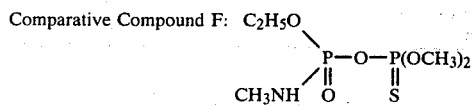

(see German DT-OS 2054189)

Comparative Compound G: 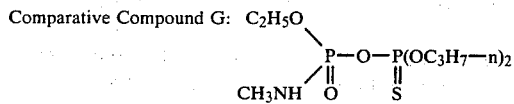

(see German DT-OS 2054189)

Comparative Compound H: 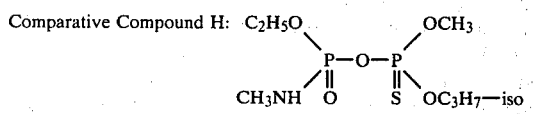

(see German DT-OS 2054189)

Comparative Compound I: 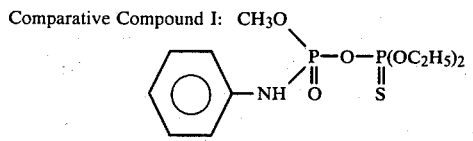

(see German DT-OS 2054189)

Comparative Compound J: 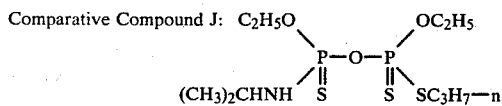

(see U.S. Pat. No. 4,110,440)

Comparative Compound K: 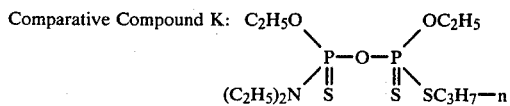

(see U.S. Pat. No. 4,110,440)

Comparative Compound L: 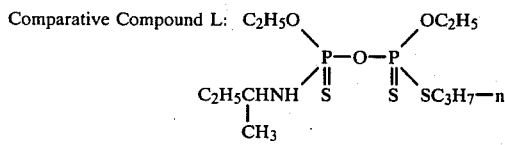

(see U.S. Pat. No. 4,110,440)

-continued

Comparative Compound M: 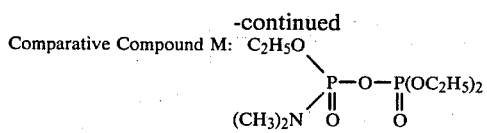

(see "Aspirantsk Roboty Nauchn" pp. 66~69 (1963))

EXAMPLE 8

This Example illustrates the test of estimating the insecticidal activity of test compounds against red flour beetle.

A sheet of filter paper placed on the bottom of a glass Petri dish of 9 cm diameter was sprayed with 1 ml of the composition under test which was prepared by diluting with water the emulsifiable concentrate of this invention made in the Example 3, to the concentration of the active compound indicated in Table 3 below. Twenty adult red flour bettles (*Tribolium castaneum*) were then placed into the dish and the dish was kept in a constant-temperature room at 25° C. 24 Hours later, the number of the dead insects was counted and % mortality was assesed. The tests were conducted with three replicates for a particular value of the concentration of the active compound under test, and the average of % mortality was calculated. The results (expressed as the averaged % mortality) are given in the Table 3 below.

TABLE 3

| Test Compounds | Mortality (%) Concentration of active compound sprayed (ppm) | |
|---|---|---|
| | 300 | 100 |
| Compound No. 1 | 100 | 100 |
| Compound No. 2 | 100 | 100 |
| Compound No. 3 | 100 | 100 |
| Compound No. 4 | 100 | 97 |
| Compound No. 5 | 100 | 97 |
| Compound No. 6 | 100 | 100 |
| Compound No. 7 | 100 | 100 |
| Compound No. 8 | 100 | 97 |
| Compound No. 9 | 100 | 90 |
| Compound No. 10 | 100 | 97 |
| Compound No. 11 | 100 | 100 |
| Compound No. 12 | 100 | 90 |
| Compound No. 13 | 100 | 100 |
| Compound No. 14 | 100 | 97 |
| Compound No. 15 | 100 | 100 |
| Compound No. 16 | 100 | 97 |
| Compound No. 17 | 100 | 90 |
| Compound No. 18 | 100 | 97 |
| Compound No. 19 | 100 | 90 |
| Comparative compound A | 100 | 60 |
| Comparative compound B | 100 | 67 |
| Comparative compound C | 73 | 40 |
| Comparative compound D | 100 | 60 |
| Comparative compound E | 100 | 57 |
| Comparative compound F | 97 | 40 |
| Comparative compound G | 100 | 58 |
| Comparative compound H | 77 | 43 |
| Comparative compound I | 83 | 40 |
| Comparative compound J | 100 | 50 |
| Comparative compound K | 100 | 65 |
| Comparative compound L | 100 | 53 |

TABLE 3-continued

| Test Compounds | Mortality (%) Concentration of active compound sprayed (ppm) | |
|---|---|---|
| | 300 | 100 |
| Comparative compound M | 100 | 50 |
| No treatment (Control) | 0 | |

EXAMPLE 9

This Example illustrates the test of estimating the effect of the test compounds for controlling "resistant" strains of green rice leafhopper.

Aquatic rice plants of an average height of about 40 cm were planted in a pot of square cross-section (6 cm×6 cm) and made of black colored polyvinyl chloride. These aquatic rice plants were treated by dusting thereon the dusting powder of this invention made in the Example 5, at the rate of application of the active compound as indicated in Table 4 below. After the dusting treatment, the treated rice plants were covered with a cylindrical box of 11 cm diameter in the cross-section and made of a polyvinyl chloride. Twenty, adult female green rice leafhoppers (*Nephotettix cincticeps*) of 3 days old after the emergence of such "resistant" strain which showed the resistance against the known organophosphorus type insecticides and against the known carbamate-type insecticides were released into and confined in the cylindrical box containing the treated aquatic rice plants. The rice plants-cultivating pot, together with the covering cylindrical box of polyvinyl chloride, was kept in a constant-temperature room at 25° C. 48 Hours after the releasing of the insects, percent of the mortality was assessed. The tests were conducted with three replicates for a particular value of the concentration of the active compound under test, and the average of % mortality was calculated. The results (expressed as averaged % mortality) are set out in Table 4 below.

TABLE 4

| Test Compounds | Mortality (%) Rate of application of active compound (g/10 ares) | |
|---|---|---|
| | 15 | 7.5 |
| Compound No. 1 | 100 | 97 |
| Compound No. 2 | 100 | 100 |
| Compound No. 3 | 100 | 100 |
| Compound No. 4 | 100 | 98 |
| Compound No. 5 | 100 | 95 |
| Compound No. 6 | 100 | 100 |
| Compound No. 7 | 100 | 100 |
| Compound No. 8 | 100 | 97 |
| Compound No. 9 | 100 | 93 |
| Compound No. 10 | 100 | 97 |
| Compound No. 11 | 100 | 100 |
| Compound No. 12 | 100 | 98 |
| Compound No. 13 | 100 | 100 |
| Compound No. 14 | 100 | 97 |
| Compound No. 15 | 100 | 100 |
| Compound No. 16 | 100 | 98 |
| Compound No. 17 | 100 | 93 |
| Compound No. 18 | 100 | 95 |
| Compound No. 19 | 100 | 93 |
| Comparative compound A | 90 | 50 |
| Comparative compound B | 73 | 47 |
| Comparative compound C | 60 | 13 |
| Comparative compound D | 67 | 33 |
| Comparative compound E | 57 | 20 |
| Comparative compound F | 60 | 43 |
| Comparative compound G | 30 | 0 |
| Comparative compound H | 57 | 23 |
| Comparative compound I | 43 | 10 |
| Comparative compound J | 87 | 20 |
| Comparative compound K | 93 | 33 |
| Comparative compound L | 90 | 37 |
| Comparative compound M | 67 | 20 |
| No treatment (Control) | 0 | |

EXAMPLE 10

This Example illustrates the test of estimating the effect of test compounds for controlling green peach aphid.

Young seedlings of egg plant were cultivated in a pot of square cross-section (6 cm×6 cm), and these young egg plants were infested with 20 adult wingless green peach aphids (*Myzus persicae*) which had been reared over some successive generations. The infested egg plant was kept in a constant-temperature room for 24 hours. After the aphids on the egg plant started to reproduce, the egg plant with the infesting green peach aphids was sprayed with the composition under test which was prepared by diluting with water the emulsifiable concentrate of this invention made in the Example 3 to the concentration of the active compound as indicated in Table 5 below. The composition was applied at the rate of 30 ml per pot. The pot was subsequently kept in a constant-temperature room at 25° C. 5 Days after the spraying, the number of the green peach aphids which was infesting the egg plant was counted, and percent of mortality was calculated. The tests were conducted with three replicates for a particular value of the concentration of the active compound under test, and the average of % mortality was calculated.

The results (expressed as averaged % mortality) are given in Table 5 below.

TABLE 5

| Test Compounds | Mortality (%) Concentration of active compound sprayed (ppm) | |
|---|---|---|
| | 100 | 50 |
| Compound No. 1 | 100 | 100 |
| Compound No. 2 | 100 | 100 |
| Compound No. 3 | 100 | 98 |
| Compound No. 4 | 100 | 94 |
| Compound No. 5 | 100 | 90 |
| Compound No. 6 | 100 | 100 |
| Compound No. 7 | 100 | 98 |
| Compound No. 8 | 100 | 94 |
| Compound No. 9 | 100 | 90 |
| Compound No. 10 | 100 | 93 |
| Compound No. 11 | 100 | 100 |
| Compound No. 12 | 100 | 94 |
| Compound No. 13 | 100 | 100 |

TABLE 5-continued

| Test Compounds | Mortality (%) Concentration of active compound sprayed (ppm) | |
|---|---|---|
| | 100 | 50 |
| Compound No. 14 | 100 | 94 |
| Compound No. 15 | 100 | 100 |
| Compound No. 16 | 100 | 98 |
| Compound No. 17 | 100 | 93 |
| Compound No. 18 | 100 | 94 |
| Compound No. 19 | 100 | 90 |
| Comparative compound A | 75 | 42 |
| Comparative compound B | 100 | 51 |
| Comparative compound C | 67 | 30 |
| Comparative compound D | 84 | 37 |
| Comparative compound E | 97 | 59 |
| Comparative compound F | 89 | 44 |
| Comparative compound G | 92 | 45 |
| Comparative compound H | 88 | 37 |
| Comparative compound I | 67 | 40 |
| Comparative compound J | 85 | 33 |
| Comparative compound K | 100 | 63 |
| Comparative compound L | 93 | 57 |
| Comparative compound M | 94 | 43 |
| No treatment (Control) | 0 | |

EXAMPLE 11

This Example illustrates the test of controlling housefly.

A sheet of filter paper was placed on the bottom of a glass Petri dish of 9 cm diameter, and the filter paper was sprayed with 1 ml of a composition under test which was prepared by diluting with water the wettable powder of this invention made in the Example 4, to a concentration of the active compound as indicated in Table 6 below. 10 Adult houseflies (*Musca domestica*) of 4 days old after the emergence were released into and confined in the covered dish. The dish containing the houseflies was kept in a constant-temperature room at 25° C. 48 Hours later, the number of dead insects was counted and % mortality was assessed. The tests were conducted with three replicates for a particular value of the concentration of the active compound under test, and the average of % mortality was calculated. The results (expressed as the averaged % mortality) are set out in Table 6 below.

TABLE 6

| Test Compounds | Mortality (%) Concentration of active compound sprayed (ppm) | |
|---|---|---|
| | 300 | 100 |
| Compound No. 1 | 100 | 100 |
| Compound No. 2 | 100 | 100 |
| Compound No. 3 | 100 | 100 |
| Compound No. 4 | 100 | 97 |
| Compound No. 5 | 100 | 93 |
| Compound No. 6 | 100 | 100 |
| Compound No. 7 | 100 | 100 |
| Compound No. 8 | 100 | 97 |

TABLE 6-continued

| Test Compounds | Mortality (%) Concentration of active compound sprayed (ppm) | |
|---|---|---|
| | 300 | 100 |
| Compound No. 9 | 100 | 93 |
| Compound No. 10 | 100 | 97 |
| Compound No. 11 | 100 | 100 |
| Compound No. 12 | 100 | 93 |
| Compound No. 13 | 100 | 100 |
| Compound No. 14 | 100 | 97 |
| Compound No. 15 | 100 | 100 |
| Compound No. 16 | 100 | 93 |
| Compound No. 17 | 100 | 90 |
| Compound No. 18 | 100 | 90 |
| Compound No. 19 | 100 | 90 |
| Comparative compound A | 77 | 50 |
| Comparative compound B | 67 | 37 |
| Comparative compound C | 47 | 10 |
| Comparative compound D | 70 | 40 |
| Comparative compound E | 63 | 23 |
| Comparative compound F | 60 | 10 |
| Comparative compound G | 43 | 7 |
| Comparative compound H | 67 | 30 |
| Comparative compound I | 47 | 0 |
| Comparative compound J | 50 | 20 |
| Comparative compound K | 83 | 37 |
| Comparative compound L | 77 | 43 |
| Comparative compound M | 87 | 30 |
| No treatment (Control) | 0 | |

EXAMPLE 12

This Example illustrates the test of estimating the effect of the new compound for controlling two-spotted spider mite.

Kidney-bean plants at the single true-leaf-extending stage planted in a pot of square cross-section (6 cm×6 cm) were infested with adult female two-spotted spider mites (*Tetranychus urticae*) which were reared over some successive generations. The number of the mites infested was 20 per pot. The infesting mites were allowed to produce the eggs on the bean plants. 24 Hours after the infestation, the bean plants and the mites were sprayed with 30 ml/pot of the composition under test which was prepared by diluting with water the wettable powder of this invention made in the Example 4 to a concentration of the active compound as indicated in Table 7 below. The treated plants in the pot were kept in a constant-temperature room at 25° C. 3 Days after the spraying, the numbers of dead mites and surviving mites were counted and the percent mortality was assessed in the same manner as in Example 10. The tests were conducted with three replicates for a particular value of the concentration of the active compound under test, and the average of mortality (%) was calculated. The results (expressed as the averaged % mortality) are given in Table 7 below.

TABLE 7

| Test Compounds | Mortality (%) Concentration of active compound sprayed (ppm) | |
|---|---|---|
| | 100 | 50 |
| Compound No. 1 | 100 | 100 |
| Compound No. 2 | 100 | 100 |
| Compound No. 3 | 100 | 99 |
| Compound No. 4 | 100 | 95 |
| Compound No. 5 | 100 | 90 |
| Compound No. 6 | 100 | 100 |
| Compound No. 7 | 100 | 100 |
| Compound No. 8 | 100 | 95 |
| Compound No. 9 | 100 | 92 |
| Compound No. 10 | 100 | 99 |
| Compound No. 11 | 100 | 100 |
| Compound No. 12 | 100 | 93 |
| Compound No. 13 | 100 | 100 |
| Compound No. 14 | 100 | 92 |
| Compound No. 15 | 100 | 100 |
| Compound No. 16 | 100 | 95 |
| Compound No. 17 | 100 | 93 |
| Compound No. 18 | 100 | 92 |
| Compound No. 19 | 100 | 90 |
| Comparative compound A | 87 | 33 |
| Comparative compound B | 78 | 30 |
| Comparative compound C | 63 | 23 |
| Comparative compound D | 82 | 63 |
| Comparative compound E | 75 | 53 |
| Comparative compound F | 60 | 25 |
| Comparative compound G | 76 | 27 |
| Comparative compound H | 73 | 38 |
| Comparative compound I | 85 | 44 |
| Comparative compound J | 66 | 37 |
| Comparative compound K | 78 | 29 |
| Comparative compound L | 82 | 50 |
| Comparative compound M | 77 | 23 |
| No treatment (control) | 0 | |

EXAMPLE 13

This Example illustrates the test under submerged condition of estimating the effect of the test compounds for controlling small brown planthopper.

Aquatic rice plants were transplanted and cultivated under the submerged condition in a pot having an area of 1/10,000 ares at the soil surface. When the aquatic rice plants so cultivated reached a 4-leave stage, the granules of this invention prepared in the Example 6 were scattered onto the surface of the submerging water where the pot was immersed. The granules were applied at the rate of application of the active compound as indicated in Table 8 below. The test plots were classified into two, the first plot was such that two days lapsed between the application of the granules and the release of the insect pests under test; and the second plot was such that 5 days lapsed between the application of the granules and the release of the insect pests. The predetermined 2 or 5 days later, the pot was covered with a cylindrical box made of a plastic resin material and having 10 cm diameter and 30 cm height. Into the box covering the pot were released and confined therein 20 adult small brown planthoppers (*Delphacodes striatella*). 48 hours after the release of the planthoppers, the number of the dead insects was counted and % mortality was assessed. The tests were conducted with three replicates for a particular value of the concentration of the active compound under test, and the average of % mortality was calculated. The results (expressed as the averaged % mortality) are set out in Table 8 below.

TABLE 8

| Test Compounds | Mortality (%) Rate of application of active compound (g/10 ares) | | | |
|---|---|---|---|---|
| | 2 Days-lapsing plot | | 5 Days-lapsing plot | |
| | 200 | 50 | 200 | 50 |
| Compound No. 1 | 100 | 100 | 100 | 93 |
| Compound No. 2 | 100 | 100 | 100 | 97 |
| Compound No. 3 | 100 | 90 | 97 | 87 |
| Compound No. 6 | 100 | 100 | 100 | 87 |
| Compound No. 11 | 100 | 100 | 100 | 93 |
| Compound No. 12 | 100 | 87 | 90 | 73 |
| Compound No. 15 | 100 | 100 | 100 | 97 |
| Compound No. 16 | 100 | 90 | 90 | 73 |
| Comparative compound A | 100 | 37 | 43 | 10 |
| Comparative compound B | 93 | 27 | 37 | 0 |
| Comparative compound C | 67 | 30 | 23 | 17 |
| Comparative compound D | 100 | 43 | 33 | 10 |
| Comparative compound E | 87 | 0 | 13 | 0 |
| Comparative compound I | 63 | 10 | 20 | 0 |
| Comparative compound J | 80 | 10 | 33 | 0 |
| No treatment (Control) | 0 | | 0 | |

EXAMPLE 14

This Example illustrates the test of estimating the effect of test compounds for controlling southern root-knot nematode.

A quantity of soil infested by sourthern root-knot nematode (*Meloidogyne incognita*) was admixed with a predetermined amount of the granules of this invention prepared in the Example 6 to such concentration of the active compound as indicated in Table 9. The mixture of the soil and the granules was stirred and mixed uniformly and then charged into a pot having an area of 1/5,000 ares. In the treated soil charged in the pot were sown 20 seeds of tomato plant per pot. The tomato seeds were cultivated in a greenhouse. 4 weeks after the seed sowing, the grown roots of the young tomato plant were withdrawn from the soil without damaging the roots, and the degree of injury of the roots was evaluated according to the following ratings to estimate the root-knot index:

Ratings of root-knot (Degree of injury)

0—No root-knot formation (perfect control).
1—Slight root-knot formation was observed at the tip of small side-roots.
2—Root-knot formation was observed in the small side-roots but the knots formed were not yet connected with each other.
3—Root-knot formation was observed along the whole length of the small side-roots with some knots being connected with each other.

4—Root-knot formation was observed in the main root, too, with the many knots in the side-roots being connected with each other.

5—The number of root-knots formed were very much great, with the knots connected with each other in the main root and also in the side-roots (corresponding to the "control" plot where no treatment was made).

Root-knot index was estimated according to the following equation:

Root-knot index (%) =

$$\frac{\Sigma(\text{Rating value} \times \text{Number of roots alloted the same rating value})}{(\text{Total number of plants under test}) \times 5} \times 100$$

The tests were conducted with three replicates for a particular value of the concentration of the active compound under test, and the average of the estimated root-knot indexes was calculated. The results (expressed as the averaged % root-knot index) are listed in Table 9 below.

TABLE 9

| Test Compound | Root-knot Index (%) Rate of application of active compound (Kg/10 ares) | |
| --- | --- | --- |
|  | 3 | .1 |
| Compound No. 1 | 0 | 9 |
| Compound No. 2 | 0 | 8 |
| Compound No. 6 | 0 | 11 |
| Compound No. 7 | 0 | 14 |
| Compound No. 11 | 0 | 9 |
| Compound No. 15 | 0 | 8 |
| Compound No. 18 | 2 | 21 |
| Comparative compound A | 12 | 62 |
| Comparative compound B | 27 | 78 |
| Comparative compound I | 20 | 63 |
| Comparative compound J | 15 | 74 |
| No treatment (Control) |  | 98 |

What we claim is:

1. The compound of the formula

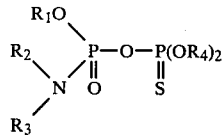

wherein $R_1$ is a lower alkyl group containing 3 or more carbon atoms and $R_2$, $R_3$ and $R_4$ may be the same or different from each other and each are a lower alkyl group.

2. A method of combating insect pests, acarine pests and/or nematode pests at a locus of infestation, which comprises treating the pests or the locus of infestation with an insecticidally, miticidally and/or nematocidally effective amount of the compound as claimed in claim 1.

3. The compound as claimed in claim 1 which is the compound of the formula

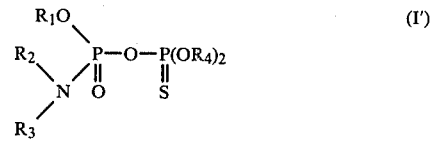

wherein $R_1$ is an alkyl group containing 3 or 4 carbon atoms and $R_2$, $R_3$ and $R_4$ may be the same or different from each other and each are an alkyl group containing 1 to 4 carbon atoms.

4. The compound as claimed in claim 1 which the compound of the formula (I) where $R_1$ is n-propyl, isopropyl, n-butyl or isobutyl, $R_2$ is methyl, ethyl or n-propyl, $R_3$ is methyl, ethyl, n-propyl, isopropyl or n-butyl, and $R_4$ is methyl, ethyl, n-propyl, isopropyl or n-butyl.

5. The compound as claimed in claim 1 which is the compound of the formula (I) where $R_1$ is n-propyl or isopropyl, $R_2$ is methyl or ethyl, $R_3$ is methyl or ethyl, and $R_4$ is ethyl.

6. The compound as claimed in claim 1 which is selected from:
Thiopyrophosphoric acid P,P-diethyl-P'-n-propyl-P'-dimethylamide (Compound No. 2);
Thiopyrophosphoric acid P,P-diethyl-P'-n-propyl-P'-methylethylamide (Compound No. 6);
Thiopyrophosphoric acid P,P-diethyl-P'-n-propyl-P'-diethylamide (Compound No. 11); and
Thiopyrophosphoric acid P,P-diethyl-P'-isopropyl-P'-diethylamide (Compound No. 13).

7. The pesticidal composition comprising as the active ingredient an insecticidally, miticidally and/or nematocidally effective amount of the compound as claimed in claim 1 of the formula

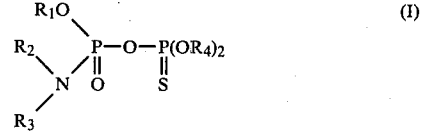

wherein $R_1$ is a lower alkyl group containing 3 or more carbon atoms and $R_2$, $R_3$ and $R_4$ may be the same or different from each other and each are a lower alkyl group, in combination with an acceptable carrier for the active ingredient.

* * * * *